United States Patent [19]

Katsuragi

[11] Patent Number: 5,469,233
[45] Date of Patent: Nov. 21, 1995

[54] OPHTHALMOLOGIC INSTRUMENT

[75] Inventor: Kenjiro Katsuragi, Tokyo, Japan

[73] Assignee: Kabushiki Kaisha Topcon, Tokyo, Japan

[21] Appl. No.: 266,530

[22] Filed: Jun. 28, 1994

[30] Foreign Application Priority Data

Jun. 29, 1993 [JP] Japan ..................... 5-159097

[51] Int. Cl.$^6$ .................. A61B 3/10; A61B 3/14
[52] U.S. Cl. .......................... 351/205; 351/208
[58] Field of Search ........................ 351/205, 208, 351/210, 214, 221; 356/237, 239

[56] References Cited

U.S. PATENT DOCUMENTS 4,813,778  3/1989  Madate et al. ................ 351/208
4,834,527  5/1989  Kobayashi ...................... 351/208

Primary Examiner—William L. Sikes
Assistant Examiner—Huy Mai
Attorney, Agent, or Firm—Finnegan, Henderson, Farabow, Garrett & Dunner

[57] ABSTRACT

A sensor 17 detects a quantity of light emitted by an alignment light source 21 and reflected by an eye. A comparison circuit 53 compares a quantity of the reflected alignment light with a predetermined quantity of reference light. If the reflected alignment light is less in quantity than the reference light, the comparison circuit 53 judges that there exist stains which exert a bad influence on the reflected alignment light. An operator obtains the judgment through a monitor 52 by which cautions are offered, so that the operator can operate an instrument in the best condition.

7 Claims, 3 Drawing Sheets

OPHTHALMOLOGIC INSTRUMENT

BACKGROUND OF THE INVENTION

1. Field of the Invention

This invention relates to an ophthalmologic instrument which includes an alignment optical system for detecting the alignment of a principal optical system of the instrument with a subject's eye.

2. Description of the Prior Art

Heretofore, an ophthalmologic instrument is known which includes an alignment optical system. In the alignment optical system, a beam of light for alignment emitted by a light source for alignment is guided to a subject's eye. The alignment light is reflected by the eye and then received by a light receiving means. Based on a state of the light received by the light receiving means, the alignment optical system detects the alignment of the principal optical system of the instrument with the eye.

A description will be given of a case where such an alignment optical system is applied to a non-contact type of tonometer as an ophthalmologic instrument. In this case, a light source to be used emits infrared rays of light. A beam of light for alignment emitted by the light source is projected onto a cornea of the eye through a jet nozzle. The alignment beam of light is reflected by the cornea and then received by the light receiving means. From a quantity of the reflected light received by the light receiving means or a point where the reflected light is received by the same, the light receiving means detects the alignment of a visual line of the eye with an optical axis of the principal optical system.

In the non-contact type of tonometer, a working distance between the eye and the jet nozzle is made short (e.g., 11 mm) enough to attain measurement accuracy.

However, such a short distance raises a problem of stains. That is, tears, fine dust, and so on are scattered from the eye by blowing air pulses from the jet nozzle toward the eye in order to make the cornea flat. Therefore, a case occurs in which part of the scattered particles adhere to optical members, such as an objective lens or the like, of the instrument and, if it is neglected to remove the part of the particles that will be a stain, the quantity of the reflected light is greatly lessened by the stain.

The decrease forms a cause of wrong operations of the instrument. The reason is that, if a beam of light different from the reflected light is received by the light receiving means at the same time together with the reflected light, a judgment on which is the alignment light is formed based on a quantity of light received by the light receiving means. Therefore, a case occurs in which, although alignment is carried out in fact, the instrument judges that the alignment is not correctly done.

SUMMARY OF THE INVENTION

It is, therefore, an object of the invention to provide an ophthalmologic instrument able to judge whether there exist stains that greatly lessen a quantity of alignment reflection light and able to work in the best condition by preventing wrong operations of the instrument.

DETAILED DESCRIPTION OF THE EMBODIMENT

The embodiment of an ophthalmologic instrument according to the invention will be hereinafter described with reference to the attached drawings.

Figure 1:
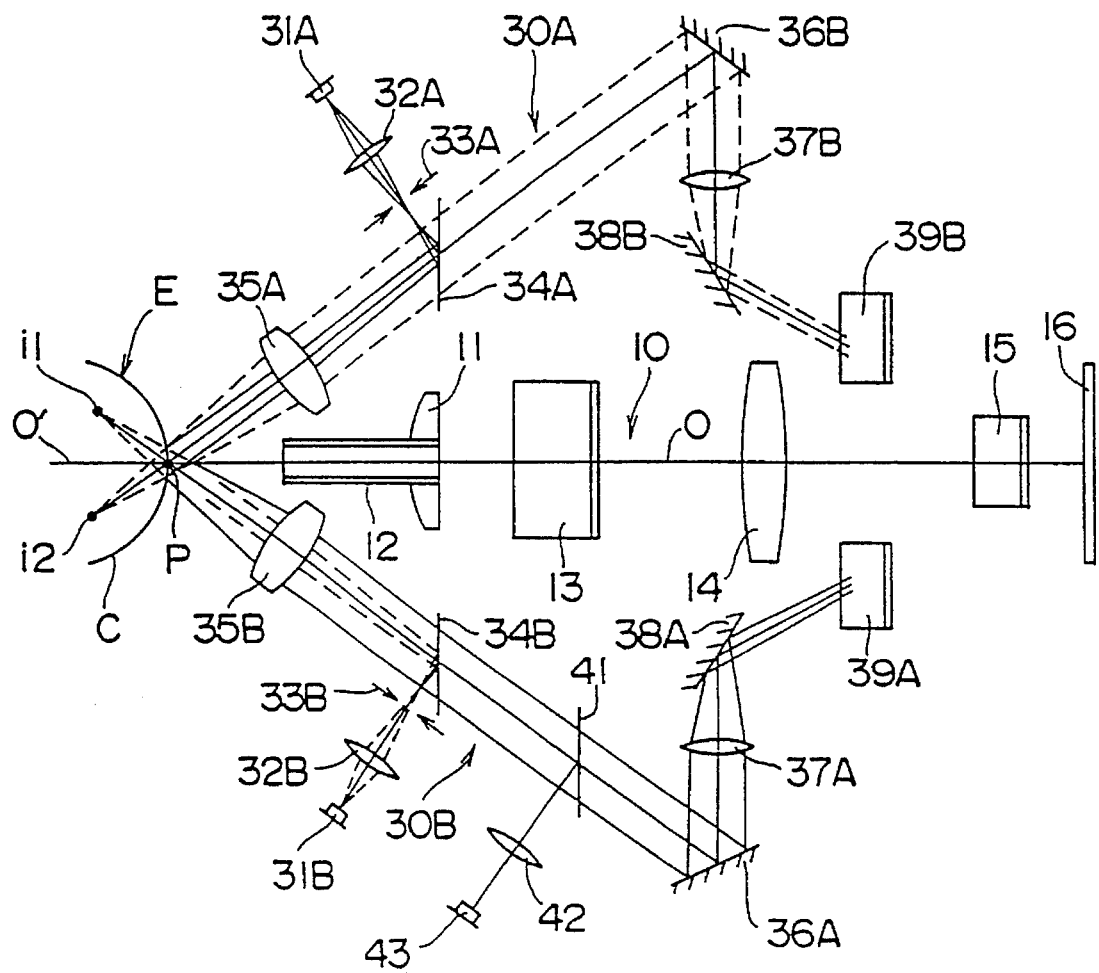
FIG. 1 is a plan view showing the optical systems of the ophthalmologic instrument according to the invention.
Figure 2:
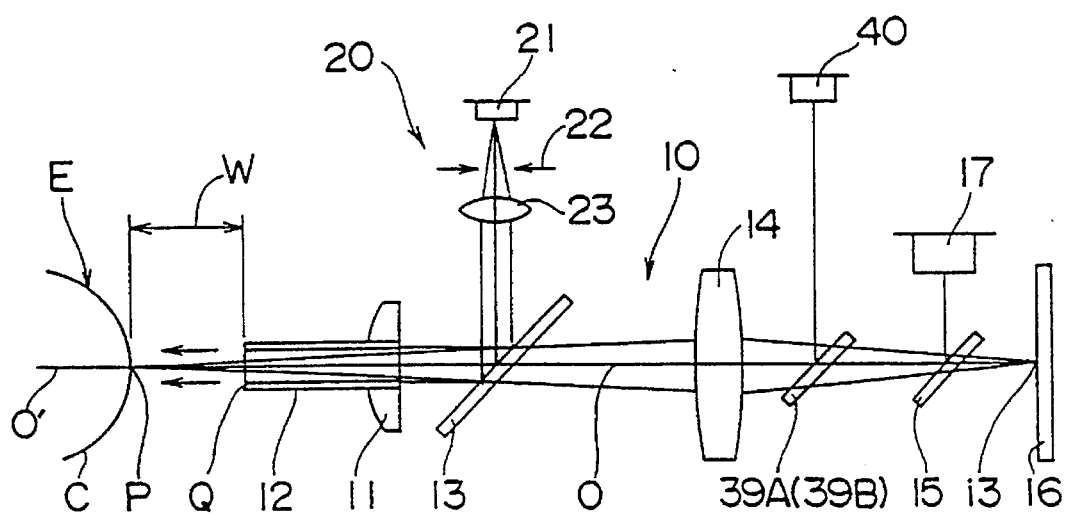
FIG. 2 is a side view showing the optical systems of the ophthalmologic instrument according to the invention.

FIGS. 1 and 2 show a mechanical arrangement of the ophthalmologic instrument.

The ophthalmologic instrument includes an anterior portion observing optical system 10 and alignment optical systems 20, 30A, and 30B. The anterior portion observing optical system 10 as a principal optical system is an optical system for observing an anterior portion of a subject's eye E as well as the E. The alignment optical system 20 is an optical system for aligning a visual line 0' of the eye E with an optical axis 0 of the anterior portion observing optical system 10 by moving an instrument body of the instrument in up, down, right, and left directions with respect to the eye E. The alignment optical systems 30A, 30B are each an optical system for setting a working distance of the instrument body with respect to the eye E.

The anterior portion observing optical system 10 includes an objective lens 11, a jet nozzle 12, an oblique half mirror 13, an image formation lens 14, a half mirror 15, and a CCD camera 16.

The jet nozzle 12 is disposed on the optical axis 0 of the objective lens 11. The jet nozzle 12 projects air pulses toward the eye E.

A beam of light for forming an image of the anterior portion of the eye E is guided to the CCD camera 16 through the objective lens 11, jet nozzle 12, oblique half mirror 13, image formation lens 14, and half mirror 15.

The alignment optical system 20 includes an LED 21 as an alignment light source, an aperture 22, a collimator lens 23, and the oblique half mirror 13.

The LED 21 emits infrared rays of light. The infrared rays of light emitted by the LED 21 pass through the aperture 22 and are made parallel rays of light by the collimator lens 23. The parallel rays of light are reflected by the oblique half mirror 13 and are projected onto a cornea C of the eye E through the jet nozzle 12. The parallel rays of light are reflected by the cornea C and become alignment reflection light. The alignment reflection light is condensed to the objective lens 11 and is guided to the image formation lens 14 and the half mirror 15.

The half mirror 15 transmits part of the alignment reflection light and reflects the other part. The alignment reflection light that has passed through the half mirror 15 is guided to the CCD camera 16 and forms an index image i3 for the alignment of the visual line 0' with the optical axis 0. On the other hand, the alignment reflection light reflected by the half mirror 15 is condensed to a light receiving sensor 17 which is used as a means for detecting a quantity of the alignment reflection light. The light receiving sensor 17 and the CCD camera 16 are conjugate to each other.

Figure 3:
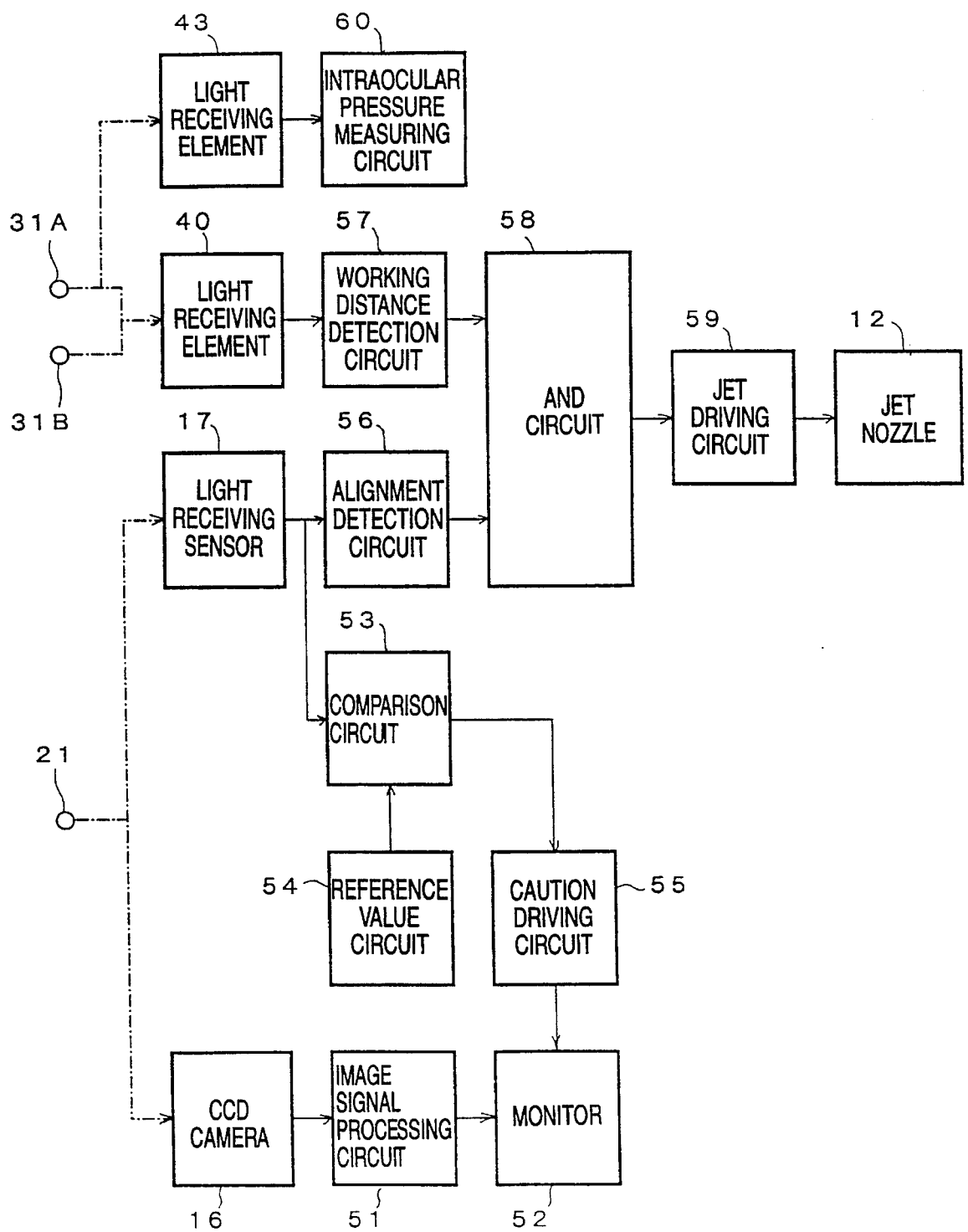
FIG. 3 is a block diagram showing circuits for controlling a quantity of light of an alignment light source of the ophthalmologic instrument according to the invention.

A reticle image (not shown) for forming a mark of an allowable area of the visual line 0' is projected onto the CCD camera 16. The anterior portion image and the index image i3 formed on the CCD camera 16 are output to an image signal processing circuit 51 shown in FIG. 3. The image signal processing circuit 51 processes and causes those images to be displayed on a monitor 52.

The quantity of the alignment reflection light is converted into an output value of, e.g., a current or a voltage. The output value is output to a comparison circuit 53 as a comparison means. Also, a reference value output by a reference value circuit 54 is output to the comparison circuit 53. The reference value is correlated with a quantity of light calculated on the basis of, e.g., the setting efficiency of the optical system ranging from the LED 21 to the light receiving sensor 17 or of a factor in the decrease of the quantity of the alignment reflection light, such as a normal reflection factor of the eye E. The comparison circuit 53 compares the output value with the reference value. By comparing the two, information is obtained about whether stains exist or not. If the output value is below the reference value, the comparison circuit 53 judges that the quantity of the alignment reflection light is greatly lessened by the stains. After that, the comparison circuit 53 outputs a caution signal to a caution driving circuit 55. The caution driving circuit 55 then outputs a caution transmission signal to the monitor 52.

The monitor 52 displays a message in letters or symbols to inform an operator of whether stains exist or not. For example, the message "THE LENS IS STAINED WITH PARTICLES OF DUST" is displayed to make a distinction between a caution against wrong operations of the instrument and a caution against stains adhering to lenses of the instrument, so that the maintenance of the instrument is facilitated.

Instead of the monitor 52 as a cautioning means, a speaker which sounds an alarm bell or an alarm lamp (indicator lamp) which emits flashing light may be used. In this case, the caution driving circuit 55 is arranged according to a cautioning means to be used. Further, a caution signal is output to the cautioning means. If the monitor 52 is used together with the speaker or the alarm lamp, the caution signal is output to both of them.

Cautioning is also carried out in a case where the decrease of the quantity of alignment reflection light is due to any cause except stains. For example, a case occurs in which an eyelash of the eye E shades the alignment reflection light. However, since the alignment is carried out through the monitor 52, information about the anterior portion of the eye E or a spot for the alignment enables the cause of the decrease of the alignment reflection light to be cleared up. Instead of the monitor 52 as a means for observing the eye E when aligning, an eyepiece or the like may be used.

The alignment optical systems 30A and 30B are disposed symmetrically with respect to the optical axis 0 of the objective lens 11. The alignment optical systems 30A and 30B serve to set a working distance W between the apex P of the cornea C and the tip Q of the jet nozzle 12 shown in FIG. 2.

The alignment optical system 30A includes an LED 31A as an alignment light source, a condenser lens 82A, an aperture 33A, a dichroic mirror 84A, objective lenses 35A and 35B, a dichroic mirror 34B, a total reflection mirror 36A, an image formation lens 37A, a total reflection mirror 38A, a half mirror 39A, a light receiving element 40, and a half mirror 41.

The LED 31A emits infrared rays of light having a wavelength of, e.g., 760 nm. The dichroic mirror 34A reflects the infrared rays having the wavelength of 760 nm and transmits infrared rays of light having a wavelength of 860 nm. A focal point of the objective lens 35A coincides with the center of the aperture 33A.

The alignment optical system 30B includes an LED 31B as an alignment light source, a condenser lens 32B, an aperture 38B, a dichroic mirror 34B, the objective lenses 35B and 35A, the dichroic mirror 34A, a total reflection mirror 36B, an image formation lens 37B, a total reflection mirror 38B, a half mirror 39B, and the light receiving element 40.

The LED 31B emits infrared rays of light having a wavelength of, e.g., 860 nm. The dichroic mirror 34B reflects the infrared rays of light having the wavelength of 860 nm and transmits infrared rays of light having the wavelength of 760 nm. Use is properly made of wavelength characteristics of the dichroic mirrors 34A and 34B according to the wavelengths of the infrared rays of light emitted by the LEDs 31A and 31B. A focal point of the objective lens 35B coincides with the center of the aperture 33B.

The infrared rays of light emitted by the LED 31A is condensed to the center of the aperture 33A by means of the condenser lens 32A. The condensed light is reflected by the dichroic mirror 34A and then is made parallel rays of light by means of the objective lens 35A. The parallel infrared rays of light are projected onto the cornea C to form an index image i1 based on the cornea specular reflection. The index image i1 is used for alignment of the working distance.

The reflected light which has formed the index image i1 is guided to the objective lens 35B. The reflected light is made parallel rays of light by means of the objective lens 35B when the focal point of the objective lens 35B coincides with the position of the index image i1. The parallel rays of light are guided to the light receiving element 40 to form an image through the dichroic mirror 34B, half mirror 41, total reflection mirror 36A, image formation lens 37A, total reflection mirror 38A, and half mirror 39A.

The infrared rays of light emitted by the LED 31B is condensed to the center of the aperture 33B by means of the condenser lens 32B. The condensed light is reflected by the dichroic mirror 34B and then is made parallel rays of light by means of the objective lens 35B. The parallel infrared rays of light are projected onto the cornea C to form an index image i2 based on the cornea specular reflection. The index image i2 is used for alignment of the working distance.

The reflected light which has formed the index image i2 is guided to the objective lens 35A. The reflected light is made parallel rays of light by means of the objective lens 35A when the focal point of the objective lens 35A coincides with the position of the index image i2. The parallel rays of light are guided to the light receiving element 40 to form an image through the dichroic mirror 34A, total reflection mirror 36B, image formation lens 37B, total reflection mirror 38B, and half mirror 39B.

When a distance between the apex P of the cornea C and the tip Q of the jet nozzle 12 is a normal working distance, the index images i1 and i2 exactly coincides with each other on the light receiving element 40, whereas, when the distance therebetween differs from the normal working distance, the index images i1 and i2 partly overlap or separate from each other.

The operator adjusts the optical axis 0 to the visual line 0' so that the index image i3 falls within an allowable area mark (a reticle image) for the visual line by operating the alignment optical system 20. Also, the operator adjusts the working distance W so that the index images i1 and i2 approximately coincide with each other. The operator carries out these adjustments by observing the monitor 52.

The alignment optical system 20 and the alignment optical systems 30A and 30b are disposed separately from each other. The reason is that an allowable area of alignment accuracy for setting the working distance W is larger than that of alignment operations for adjusting the visual line 0' to the optical axis 8. Therefore, the separation of the alignment optical system 20 from the alignment optical systems 30A and 30b enables the alignment operations to be easily performed.

A group of the LED 31A, condenser lens 32A, aperture 33A, dichroic mirror 34A, and objective lens 35A serves as an optical system for projecting detection light onto the cornea C in order to optically detect the deformation of the cornea C caused by blowing air pulses onto the cornea C from the jet nozzle 12. The cornea C is made flat by the air pulses.

The air pulses are jetted from the jet nozzle 12 according to a jet signal output by a jet driving circuit 59. The jet signal is output in the following manner. An alignment detection circuit 56 first detects an image formation state made on the light receiving sensor 17 and, at the same time, a working distance detection circuit 57 detects an image formation state of the index images i1 and i2. Alignment OK signals are then output from the circuits 56 and 57 to an AND circuit 58 if the image formation states are judged OK by the circuits 56 and 57. The AND circuit 58 that has received the alignment OK signals outputs a jet OK signal to the jet driving circuit 59. According to the jet OK signal, the jet driving circuit 59 outputs a jet signal to the jet nozzle 12.

On the other hand, the light reflected by the cornea C that is made flat by blowing the air pulses is guided to the half mirror 41 through the objective lens 35B and the dichroic mirror 34B. The reflected light is directed toward a relay lens 42 by the half mirror 41 and is condensed to the light receiving element 43 by the relay lens 42.

A group of the objective lens 35B, dichroic mirror 34B, half mirror 41, relay lens 42, and light receiving element 43 serves as an optical system for receiving the reflected light and detecting the deformation of the cornea C. That is, the more the cornea C is deformed, the more the light receiving element 43 receives the light reflected by the cornea C. Under a well-known process, an intraocular pressure measuring circuit 60 measures the intraocular pressure of the eye E in the basis of the increase of a quantity of the light received by the element As mentioned above, in the ophthalmologic instrument according to the invention, whether there exist stains by which the quantity of alignment reflection light is lessened below a predetermined quantity of reference light is judged by comparing the quantity of the alignment reflection light detected by a reflection light detecting means with the predetermined quantity of the reference light. If such stains are detected, a cautioning means alarms an operator. Therefore, the operator can judge whether the stains exist or not, thus operating the instrument in the best condition.

What is claimed is:

1. An ophthalmologic instrument comprising:

an alignment optical system for detecting an alignment of a principal optical system with a subject's eye in a way that alignment light emitted by an alignment light source is guided to the eye, is reflected thereby, and is received by a light receiving means;

means for detecting a quantity of the reflected alignment light received by said light receiving means;

means for comparing the quantity of the reflected alignment light detected by said detecting means with a predetermined quantity of reference light; and means for warning an operator of the reflected alignment light being less in quantity than the reference light if said comparing means judges that the quantity of the reflected alignment light is less than the predetermined quantity of the reference light.

2. An ophthalmologic instrument according to claim 1, wherein said comparing means compares the predetermined quantity of the reference light with the quantity of the reflected alignment light obtained when the alignment is completed.

3. An ophthalmologic instrument according to claim 1, wherein said light receiving means judges completion of the alignment of the principal optical system with the eye by a position of an image of the reflected alignment light.

4. An ophthalmologic instrument comprising:

a first alignment optical system for detecting upward, downward, rightward, and leftward alignments of a principal optical system with a subject's eye in a way that alignment light emitted by an alignment light source is guided to the eye, is reflected thereby, and is received by a light receiving means;

a second alignment optical system, disposed independently of said first alignment optical system, for detecting a working distance between the principal optical system and the eye in a way that alignment light emitted by an alignment light source is guided to the eye, is reflected thereby, and is received by a light receiving means;

means for detecting a quantity of the reflected alignment light;

means for comparing the quantity of the reflected alignment light detected by said detecting means with a predetermined quantity of reference light; and means for warning an operator of the reflected alignment light being less in quantity than the reference light if said comparing means judges that the quantity of the reflected alignment light is less than the predetermined quantity of the reference light.

5. An ophthalmologic instrument according to claim 4, wherein said comparing means compares the predetermined quantity of the reference light with the quantity of the reflected alignment light obtained when the alignment in said first or second optical system is completed.

6. An ophthalmologic instrument according to claim 4, wherein said light receiving means of said first optical system judges completion of the upward, downward, rightward, and leftward alignments of the principal optical system with the eye by a position of an image of the reflected alignment light.

7. An ophthalmologic instrument according to claim 4, wherein said second optical system comprises a pair of optical systems wherein the alignment light is guided obliquely to the eye and the reflected light is guided obliquely from the eye, and said light receiving means of said second optical system detects completion of an adjustment of the working distance when each of the reflected alignment light guided by the pair of optical systems coincides with the other.

\* \* \* \* \*